United States Patent [19]

Toda et al.

[11] 4,374,292

[45] Feb. 15, 1983

[54] PROCESS FOR PREPARING α-THUJENE

[75] Inventors: Haruhiko Toda, Odawara; Moriaki Higo, Kanagawa; Hitoshi Saga, Hadano; Masafu Shinbo, Odawara, all of Japan

[73] Assignee: Lion Corporation, Tokyo, Japan

[21] Appl. No.: 345,430

[22] Filed: Feb. 3, 1982

[30] Foreign Application Priority Data

Feb. 3, 1981 [JP] Japan .................................. 56-14762

[51] Int. Cl.³ .............................................. C07C 2/76
[52] U.S. Cl. ...................................... 585/360; 585/947
[58] Field of Search ................................ 585/360, 947

[56] References Cited

U.S. PATENT DOCUMENTS

| | | | |
|---|---|---|---|
| 3,278,623 | 10/1966 | Derfer | 585/947 |
| 3,678,119 | 7/1972 | Kitchens et al. | 585/360 |
| 3,681,470 | 8/1972 | Kitchens et al. | 585/360 |
| 3,974,103 | 8/1976 | Kaiser | 585/947 |

OTHER PUBLICATIONS

Chem. Abs., 62, 6515d, (1965).
Alberto Ferro et al., *Helv. Chim. Acta.*, 57, 1152–1155, (1974).
Shrinivas P. Acharya et al., *J. Org. Chem.*, 34, 3015–3023, (1969).
N. N. Joshi et al., Tetrahedron, 20, 2911–2919, (1964).

*Primary Examiner*—Curtis R. Davis
*Attorney, Agent, or Firm*—Birch, Stewart, Kolasch & Birch

[57] ABSTRACT

α-Thujene is prepared in high yields by isomerizing 1 mole of sabinene with 0.2 to 0.5 moles of an alkali metal, preferably lithium and 0.3 to 0.8 moles of a primary or secondary amine, preferably ethylenediamine. Formation of by-products such as p-cymene is minimized.

2 Claims, No Drawings

PROCESS FOR PREPARING α-THUJENE

BACKGROUND OF THE INVENTION

This invention relates to a process for preparing α-thujene.

α-Thujene is the typical starting material from which sabinene hydrate, known as a useful flavor component, is prepared. One of the prior art processes for preparing α-thujene is the isomerization of sabinene in the presence of ethylenediaminolithium which is obtained by the reaction of lithium with ethylenediamine (see, for example, Shrinivas P. Acharya et al., *J. Org. Chem.*, 34, 3015 (1969) and Alberto Ferro et al., *Helv. Chim. Acta.*, 57, 1152 (1974)).

Such a prior art process, however, has the disadvantage that isomerization of sabinene into α-thujene is accompanied with a relatively large amount of by-products such as p-cymene. It is troublesome to isolate α-thujene from such a reaction mixture. If the reaction mixture is directly used without isolation of α-thujene at this stage as a starting material for the synthesis of sabinene hydrate, troublesome isolation must be done at an intermediate or final stage. In either case, these working problems result in reduced yields of α-thujene or an end product available from α-thujene.

SUMMARY OF THE INVENTION

It is, therefore, an object of the present invention to provide a process for efficient and effective isomerization of sabinene into α-thujene in a high yield while minimizing the formation of by-products.

Making researches on the preparation of α-thujene by isomerizing sabinene with an alkali metal such as lithium and a primary or secondary amine, the inventors have found that sabinene, the alkali metal and the amine should be present in critical proportions in order to minimize the formation of by-products.

According to the present invention, there is provided a process for preparing a α-thujene by isomerizing sabinene with an alkali metal and a primary or secondary amine, wherein 0.2 to 0.5 moles of the alkali metal and 0.3 to 0.8 moles of the primary or secondary amines are used per mole of sabinene.

In the above-referred process by Shrinivas P. Acharya, 1.6 moles of lithium and 7.2 moles of ethylenediamine are used per mole of sabinene. In the process by Albert Ferro, 1 mole of lithium and 3.5 moles of ethylenediamine are used per mole of sabinene. The alkali metal and primary or secondary amine are used in larger molar amounts than sabinene as in the processes referred above, a relatively large amount of by-products, particularly, p-cymene form. The inventors have found that if the molar numbers of the alkali metal and the primary or secondary amine are less than that of sabinene, more specifically, if 1 mole of sabinene is reacted with 0.2 to 0.5 moles of the alkali metal and 0.3 to 0.8 moles of the primary or secondary amine, by-products form in a minimum amount, and particularly, little or no p-cymene forms. The resulting reaction mixture is relatively easy to isolate α-thujene. Furthermore, even when thus prepared α-thujene in the form of a crude reaction product is used to prepare sabinene hydrate without isolation, intermediate or end products may be easily isolated. Consequently, α-thujene, and hence, the end product obtained from α-thujene may be produced in high yields.

DETAILED DESCRIPTION OF THE INVENTION

The above and other objects, features and advantages of the invention will become more apparent from the accompanying description.

Sabinene which is the starting material in the process of the present invention may be prepared by any suitable well-known process. Alternatively, essential oils containing sabinene, for example, nutmeg oil particularly when (+)-sabinene is required, may equally and advantageously be used. In the latter case, nutmeg oil may be vacuum distilled, for example, at 65°–90° C. and 30 mmHg, to remove 4-terpineol, myristicin and other undesired components. Thus distilled oil (to be referred to as "sabinene oil," hereinafter) is the preferred starting material.

According to the present invention, sabinene in pure or oil form is isomerized with an alkali metal and a primary or secondary amine into α-thujene. The alkali metals used herein include lithium, sodium, potassium, etc., alone or in admixture, with lithium being most preferred. The primary and secondary amines used herein may be either monoamines or polyamines, for example, diamines and triamines, and specifically, include n-hexylamine, n-heptylamine, 2-aminoheptane, 2-methyl-4-aminopentane, cyclopentylamine, cyclohexylamine, di-n-propylamine, ethyl-n-butylamine, isopropyl-n-butylamine, ethylenediamine, 1,2-diaminopropane, 1-dimethylamino-2-aminopropane, diethylenetriamine and the like, alone or in admixture of two or more. The most preferred amine is ethylenediamine.

In the practice of the present invention, the alkali metal is used in an amount of 0.2 to 0.5 moles, particularly, 0.2 to 0.3 moles and the primary or secondary amine is used in an amount of 0.3 to 0.8 moles, particularly, 0.4 to 0.6 moles per mole of sabinene. By limiting the molar numbers of the alkali metal and the primary or secondary amine to the above-defined ranges which are less than the molar number of sabinene, the present invention allows sabinene to be isomerized into α-thujene with minimized formation of by-products. It is to be noted that a major portion of sabinene is converted into α-thujene while a minor portion of the sabinene is not converted into other compounds and remains unchanged. After the reaction, the unchanged sabinene may be recovered for reuse as the starting material. Consequently, the present invention has an additional advantage that the loss of the starting sabinene is minimized. On the contrary, if the molar numbers of the alkali metal and the primary or secondary amine are larger than the molar number of sabinene, a relatively large amount of by-products form, failing to attain the object of the present invention. An additional disadvantage is that an extraction solvent such as pentane is required in treatments of the reaction mixture. With the use of the alkali metal and the amine in smaller molar proportions than the starting sabinene according to the present invention, α-thujene oil may be obtained simply by washing the reaction mixture with water. Extraction with a solvent is not necessarily needed. Therefore, the process of the present invention provides a reaction mixture which is very simple to work up, achieving a substantial cost reduction.

It is preferred in the practice of the present invention that the alkali metal and the primary or secondary amine are previously heated to react in an atmosphere of air, nitrogen or the like to form an alkali metal amide which is then used in the isomerization of sabinene. For instance, lithium and ethylenediamine are previously reacted at a temperature of 90° to 140° C. in an atmosphere of air, nitrogen or the like, and the resulting ethylenediaminolithium is used to isomerize sabinene. This allows more efficient isomerization.

The isomerization reaction of sabinene may be effected in the presence or absence of a solvent, preferably a nonpolar solvent such as n-octane, n-nonane, xylene, α-pinene, etc. Although the isomerization of sabinene may be effected at room temperature, heating at a temperature of 120° to 160° C. is preferred. The reaction time usually ranges from 3 to 8 hours.

After the isomerization, α-thujene oil may be obtained through suitable post-treatments. The reaction mixture is cooled down to room temperature and poured into ice-cold water to decompose the alkali metal amide. Then, an organic phase is separated from the water phase directly or optionally by adding thereto an organic solvent, preferably a water-insoluble solvent such as ethers, benzene, hydrocarbons, etc., for separation. The organic phase is washed with water and dried, affording α-thujene oil. This α-thujene oil may be further purified by vacuum distillation.

Thus obtained α-thujene in a purified form or α-thujene oil form may be used as a starting material for producing sabinene hydrate. Particularly, α-thujene oil which is obtained by isomerization of the sabinene oil distilled from nutmeg oil according to the present invention is the best starting material for the production of trans-sabinene hydrate.

A typical example of the method for producing trans-sabinene hydrate from α-thujene will be described below.

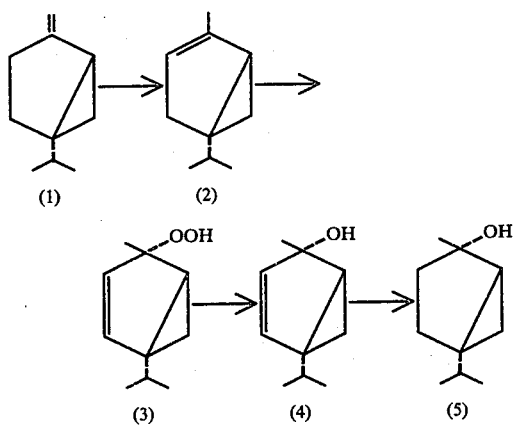

(A)

As shown in sequence (A), (+)-sabinene (1) is isomerized into (−)-α-thujene (2), which is subjected to photosensitized oxygenation to form (+)-trans-4-hydroperoxy-β-thujene (3), which is converted into (+)-trans-4-hydroxy-β-thujene (4), which is catalytically hydrogenated to form (+)-trans-sabinene hydrate (5).

The photosensitized oxygenation of α-thujene may be effected in the present or absence of a solvent. Examples of the solvent, when used, are methanol, ethanol, n-propanol, isopropanol, butanol, n-pentane, n-hexane, cyclohexane, petroleum ether, ligroin, benzene, toluene, acetone, methyl ethyl ketone, diethyl ether, dioxane, ethylene glycol, dichloromethane, chloroform, carbon tetrachloride, dichloroethane, trichloroethane, tetrachloroethane, ethyl acetate, butyl acetate, pyridine, piperazine or the like, or optionally, in admixture with water. Also included are mixtures of two or more of the above-said solvents. The most preferred solvent is methanol because of its high efficiency, low cost, low boiling point and easy handling. The light source used in the photosensitized oxygenation may include low-, and high-pressure mercury lamps, tungsten lamps, halogen lamps, high pressure xenon lamps and other lamps which are commonly used in photosensitized oxygenation. Irradiation may be carried out by either external or internal method. Furthermore, a sensitizer may be used upon photosensitized oxygenation of α-thujene. Any suitable sensitizers which are usually employed in photosensitized oxygenation may be used, including phthalein dyestuffs such as Rose bengale, Erythrosine and eosine, thiazine dyestuffs such as methylene blue, porphyrin dyestuffs such as chlorophyll-a and -b, and hematoporphyrin, acridine dyestuffs such as acridine orange, and other dyestuffs, for example, anthraquinone, benzoquinone, rhodamine B, fluorescein, anthracene, pyrene and its derivatives, zinc tetraphenyl-porphyrin and the like. These sensitizers may be added in amounts of about 0.01 to 100%, preferably 0.5 to 10% by weight based on the weight of α-thujene.

The above-mentioned photosensitized oxygenation may preferably be effected under alkaline conditions in the range of pH 7 to 12 which is attained by adding an alkali, for example, an alkali metal hydroxide such as sodium hydroxide, potassium hydroxide, and lithium hydroxide. The alkali is added in effective amounts of 1% or less based on the weight of α-thujene. The addition of alkali prevents the sensitizer from being decomposed, and thus contributes to a substantial reduction of the amount of the sensitizer to about 1/5 or less of the amount of the sensitizer required in the absence of alkali, achieving an easy purification and a considerable cost reduction. The photosensitized oxygenation may preferably be carried out at a temperature of 0° to 50° C. for a period of 2 to 36 hours.

After the photosensitized oxygenation is complete, the sensitizer may be extracted out from the reaction mixture. Although trans-4-hydroperoxy-β-thujene may be isolated from the reaction mixture as by vacuum distillation, if needed, the reaction mixture may advantageously be passed to the subsequent reduction step without isolation.

Trans-4-hydroperoxy-β-thujene may be reduced into trans-4-hydroxy-β-thujene by adding the former to a solution of a reducing agent such as sodium sulfite, sodium hydrogensulfite, thiourea, potassium iodide-acetic acid, triphenyl phosphine, trialkyl phosphites, sodium boron hydride, lithium aluminum hydride, zinc-acetic acid, etc., preferably over a period of 3 hours to a few days at a temperature of 20° C. or lower. This hydroxy derivative may also be obtained by catalytic reduction or alkali decomposition of trans-4-hydroperoxy-β-thujene.

After the reduction, the reaction mixture may preferably be subjected to extraction with a suitable organic solvent such as benzene and ether. The solvent is then distilled off from the extraction liquor and trans-4-hydroxy-β-thujene is purified by further distillation before it is subjected to the final catalytic hydrogenation. Particularly, trans-sabinene hydrate may advantageously be synthesized from nutmeg oil by allowing a sequence of reactions to proceed without a special isolating step the successive reactions and carrying out an isolating/purifying treatment only after the reaction of trans-4-hydroperoxy-β-thujene to trans-4-hydroxy-β-thujene. This leads to simple operation and increased yield. The isolating/purifying treatment may be carried out by precise distillation, liquid-liquid extraction or the like.

The procedure of catalytic hydrogenation of trans-4-hydroxy-β-thujene to synthesize trans-sabinene hydrate may be carried out in the presence or absence of a solvent. The solvent may be selected from those solvents described earlier for the photosensitized oxygenation of α-thujene, with methanol being preferred.

The catalysts which can be used in the catalytic hydrogenation of trans-4-hydroxy-β-thujene include Raney nickel, Urushibara nickel, colloidal palladium, platinum black, platinum oxide, nickel sulfide, etc. Among them, Raney nickel and Urushibara nickel are most preferred because of their increased catalytic activity and low cost. These catalysts may generally be added in amounts of about 5 to 200%, preferably 5 to 10% by weight based on the weight of trans-4-hydroxy-β-thujene. In this catalytic hydrogenation, hydrogen may be used either at atmospheric pressure or under pressure. Higher the hydrogen pressure and larger the amount of the catalyst, sooner the reaction terminates. Generally, the reaction time is 1 to 2.5 hours and the reaction temperature is 0° to 45° C.

After the catalytic reaction is complete, trans-sabinene hydrate may be recovered by removing the catalyst from the reaction mixture by filtration, distilling off the solvent, and fractionally distilling the residue in vacuum, optionally followed by further purification, all in a conventional manner. It is to be understood that the trans-sabinene hydrate products including those obtained by vacuum distillation of said residue and purified one obtained by further purification thereof may be used in any desired applications, for example, as a flavor component for dentifrices, food and drink, particularly as an agent for enhancing the flavor of peppermint and spearmint.

The process of the present invention for preparing α-thujene by isomerizing sabinene with an alkali metal and a primary or secondary amine is characterized by the use of 0.2 to 0.5 moles of the alkali metal and 0.3 to 0.8 moles of the primary or secondary amine per mole of sabinene and has the advantage of little or no formation of by-products such as p-cymene. The reaction mixture is easy to isolate or purify. Particularly, the subsequent reactions, for example, toward the synthesis of trans-sabinene hydrate, may efficiently and advantageously proceed with α-thujene prepared without special purification, and purification of intermediates or the final product is easy to carry out at any given stages. And desired end product, for example, trans-sabinene hydrate may be efficiently produced in relatively high yields.

To further illustrate the present invention, and not by way of limitation, the following examples are given.

EXAMPLE 1

1.80 g (0.26 moles) of lithium and 29.45 g (0.49 moles) of ethylene diamine were reacted in air at 110° C. for 40 minutes, and then combined with 302.06 g of sabinene oil obtained by simple distillation of nutmeg oil and containing 45.1% of (+)-sabinene (1.0 mole (+)-sabinene). The mixture was moderately refluxed for 4.5 hours at a temperature of 150° C.

After the reaction was complete, the reaction mixture was cooled to room temperature and then poured into 240 ml of ice-cold water. The oily phase was separated by means of a separatory funnel, washed four times each with 120 ml of water, and dried to give 299.71 g of α-thujene oil containing 40.0% of α-thujene. The yield of α-thujene was 88%.

The products and their yields are shown in Table 1 together with the previously reported data.

TABLE 1

| | Reactants (molar ratio) | | | Reaction Condition | | Products | | | |
|---|---|---|---|---|---|---|---|---|---|
| | Sabinene | Lithium | Ethylene-diamine | Temperature | Time | α-Thujene | Sabinene | p-Cymene | Others |
| Example 1 | (+)1.0 | 0.26 | 0.49 | 150° C. | 4.5 hrs. | (−)88% | 12% | 0% | — |
| Control 1 | (+)1.0 | 4.7 | 20.4 | reflux | 9 hrs. | — | — | 87% | 13% |
| Control 2 | (+)1.0 | 1.6 | 7.2 | room temp. | 1 day | (−)68% | 7% | 25% | — |
| Control 3 | (+)1.0 | 1.0 | 3.5 | 110° C. | 5 hrs | (−)5.4% | — | 94.6% | — |

Note 1
Control 1: N. N. Joshi et al., Tetrahedron, 20, 2911 (1964)
Control 2: Shrinivas P. Acharya et al., J. Org. Chem., 34, 3015 (1969)
Control 3: Alberto Ferro et al., Helv. Chim. Acta., 57, 1152 (1974)
Note 2
(+)in the column of sabinene designates (+)-sabinene.
(−)in the column of α-thujene designates (−)-α-thujene.
Note 3
Controls start from pure sabinene.

As seen from the data of Table 1, according to the present invention, α-thujene can be formed in a high yield without a by-product or p-cymene. It is to be noted that p-cymene forms as a result of decomposition of sabinene or α-thujene. It is therefore desired to avoid the formation of p-cymene in order to carry out the efficient reaction.

EXAMPLE 2

500 g of nutmeg oil containing 35.5% of (+)-sabinene was subjected to distillation at 65°–95° C. and 30 mmHg, obtaining 408 g of sabinene oil containing 43.5% of (+)-sabinene.

0.48 g (69 millimoles) of lithium and 9 g (150 millimoles) of ethylenediamine were reacted in the atmosphere of air at a temperature of 128°–133° C. for 4 hours, and then mixed with 82 g of the above-prepared sabinene oil containing 35.7 g (262 millimoles) of (+)-sabinene. The mixture was allowed to react for 6 hours at 130° C. The reaction mixture was treated as described in Example 1 and thereafter, subjected to distillation at 60°–75° C. and 30 mmHg, affording 56.8 g of α-thujene oil containing 47.8% of (−)-α-thujene. The yield of (−)-α-thujene was 76.0%.

In this example, p-cymene was not formed.

EXAMPLE 3

10.3 g (0.45 moles) of sodium and 91.1 g (0.9 moles) of di-n-propylamine were reacted in a nitrogen atmosphere for 30 minutes at 90° C., and then mixed with 453.1 g of sabinene oil containing 45.1% of (+)-sabinene (1.5 moles (+)-sabinene) as used in Example 1. The mixture was gently refluxed for 4 hours at a temperature of 120° C.

After the reaction was complete, a post-treatment was carried out as in Example 1, giving 445.8 g of α-thujene oil containing 33.0% of α-thujene. Yield 72%.

In this example, p-cymene was not formed.

A further example is set forth to illustrate the preparation of trans-sabinene hydrate from (−)-α-thujene.

EXAMPLE 4

Synthesis of (+)-trans-4-hydroxy-β-thujene

To 16 g of the α-thujene oil obtained in Example 2 and containing 7.65 g (56.2 millimoles) of (−)-α-thujene were added 32 g of methanol, 0.08 g (2.0 millimoles) of sodium hydroxide, and 50 mg of Rose bengale as a sensitizer. This mixture was irradiated at a temperature of 22°–28° C. for 2 hours with a 100 Watt high-pressure mercury lamp while introducing oxygen at a flow rate of 20 to 30 ml/min.

Thereafter, the reaction solution containing (+)-trans-4-hydroperoxy-β-thujene was added to 25 g of sodium sulfite in 125 g of water. The mixture was stirred for 3 hours at a temperature of 20° C. or lower, and then extracted with benzene. The benzene was distilled off from the extraction liquor, obtaining 14.3 g of a crude product containing 35.1% of (+)-trans-4-hydroxy-β-thujene. The yield of (+)-trans-4-hydroxy-β-thujene was 58.7%. Thereafter, this crude product was distilled at 88°–91° C. and 30 mmHg, to afford 3.75 g of a purified product containing 84% of (+)-trans-4-hydroxy-β-thujene. The isolated yield of (+)-trans-4-hydroxy-β-thujene was 36.8%.

When the above-mentioned photosensitized oxygenation was effected in the absence of sodium hydroxide, the amount of Rose bengale should be increased to 250 mg to effect the reaction to an equal extent. It was found that the amount of the catalyst can be considerably reduced by adding sodium hydroxide.

Synthesis of (+)-trans-sabinene hydrate

To 22.8 g of the distillation purified product containing 19.2 g (126 millimoles) of (+)-trans-4-hydroxy-β-thujene were added 75 g of methanol and 1.0 g of Raney nickel as a hydrogenation catalyst. The reaction was effected at a temperature of 30°–45° C. under a hydrogen pressure of 10 kg/cm$^2$ (total hydrogen volume 5 liters).

Thereafter, the Raney nickel was filtered off from the reaction solution, the methanol was distilled off in vacuum, and the residue was fractionally distilled in vacuum (20 mmHg), giving 18.6 g of a purified product containing 93% of (+)-trans-sabinene hydrate having a boiling point of 90°–95° C./20 mmHg. The yield of (+)-trans-sabinene hydrate was 88.9%.

What is claimed is:

1. A process for preparing α-thujene by isomerizing sabinene with an alkali metal and a primary or secondary amine, the improvement comprising using 0.2 to 0.5 moles of the alkali metal and 0.3 to 0.8 moles of the primary or secondary amine per mole of the sabinene.

2. A process according to claim 1 wherein the alkali metal is selected from the group consisting of lithium, sodium, potassium, and mixtures thereof, and the amine is selected from the group consisting of n-hexylamine, n-heptylamine, 2-aminoheptane, 2-methyl-4-aminopentane, cyclopentylamine, cyclohexylamine, di-n-propylamine, ethyl-n-butylamine, isopropyl-n-butylamine, ethylenediamine, 1,2-diaminopropane, 1-dimethylamine-2-aminopropane, diethylenetriamine and mixtures thereof.

* * * * *